US009492488B2

(12) United States Patent
Trachtman

(10) Patent No.: US 9,492,488 B2
(45) Date of Patent: *Nov. 15, 2016

(54) COMPOSITIONS AND METHOD FOR TREATMENT AND PROPHYLAXIS OF INFLAMMATORY BOWEL DISEASE

(71) Applicant: Ira Milton Trachtman, Sherman, CT (US)

(72) Inventor: Ira Milton Trachtman, Sherman, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/857,933

(22) Filed: Sep. 18, 2015

(65) Prior Publication Data

US 2016/0000839 A1 Jan. 7, 2016

Related U.S. Application Data

(63) Continuation of application No. 13/517,486, filed as application No. PCT/US2010/062339 on Dec. 29, 2010, now Pat. No. 9,138,441.

(60) Provisional application No. 61/291,474, filed on Dec. 31, 2009.

(51) Int. Cl.
| | | |
|---|---|---|
| *A61K 35/741* | (2015.01) | |
| *A61K 35/747* | (2015.01) | |
| *A61K 9/24* | (2006.01) | |
| *A61K 45/06* | (2006.01) | |
| *A61K 31/505* | (2006.01) | |
| *A61K 35/745* | (2015.01) | |
| *A61K 31/63* | (2006.01) | |
| *A61K 31/635* | (2006.01) | |
| *A61K 36/064* | (2006.01) | |
| *A61K 35/00* | (2006.01) | |

(52) U.S. Cl.
CPC .............. *A61K 35/741* (2013.01); *A61K 9/209* (2013.01); *A61K 31/505* (2013.01); *A61K 31/63* (2013.01); *A61K 31/635* (2013.01); *A61K 35/745* (2013.01); *A61K 35/747* (2013.01); *A61K 36/064* (2013.01); *A61K 45/06* (2013.01); *A61K 2035/115* (2013.01)

(58) Field of Classification Search
None
See application file for complete search history.

(56) References Cited

U.S. PATENT DOCUMENTS

| 7,018,629 B2 | 3/2006 | Jacob et al. |
| 2003/0031659 A1 | 2/2003 | Farmer |
| 2007/0060552 A1 | 3/2007 | Ekwuribe et al. |
| 2011/0240512 A1 | 10/2011 | Dorfner |
| 2012/0214833 A1 | 8/2012 | Kuklarni et al. |

FOREIGN PATENT DOCUMENTS

| DK | WO 2007036230 A1 * | 4/2007 | ........... A61K 31/685 |
| EE | WO 2009092810 A2 * | 7/2009 | ............. A61K 9/209 |
| WO | 2004069156 A1 | 8/2004 | |
| WO | 2009134948 A1 | 11/2009 | |
| WO | 2009158384 A1 | 12/2009 | |
| WO | 2011082218 A1 | 7/2011 | |

OTHER PUBLICATIONS

J. Fallingborg, "Intraluminal pH of the human gastrointestinal tract," Dan Med Bull. Jun. 1999; 46(3):183-96. (Abstract only).*
Campieri Massimo et al.: "Combination of antibiotic and probiotic treatment is efficacious in prophylaxis of post-operative recurrence of Crohn's disease: A Randomized controlled study vs. mesalamine", Gastroenterology; 101st annual meeting of the American Gastroenterological Associate and the Digestive Disease Week, San Diego, CA, US; May 21-24, 2000, Elsevier, Philadelphia, PA, vol. 118, No. 4 part 1, pp. AGAA781 (2000).
Danzi JT: "Trimethoprim-Sulfamethoxazole in the Therapy of Severe Ulcerative Colitis and Crohn;s Disease", American Journal of Gastroenterology, vol. 82, No. 9, pp. 960 (1987).
Dubinsky, MC., "Azathioprine, 6-mercaptopurine in inflammatory bowel disease: pharmacology, efficacy, and safety (Abstract)", Clin Gastroenterol Hepatol., vol. 2, No. 9, pp. 731-743 (2004).
Ecology Health Center, "Fatty Acids for the Treatment of Crohn's Disease," <http://www.crohns.net/Miva/education/articles/Fatty_Acids_for_the_Treatment_of_Crohns_Disease.shtml>, pp. 1-2 (2005).
Feagan Brian G: "Maintenance therapy for inflammatory bowel disease", American Journal of Gastroenterology, Elsevier Science Inc., US, vol. 98, No. 12 Supplement, pp. S6-S17 (2003).
Hudson M J et al.: "The Microbial Flora of the Rectal Mucosa and Feces of Patients with Crohns Disease before and during Antimicrobial Chemotherapy", Journal of Medical Microbiology, vol. 18, No. 3, pp. 335-346 (1984).
International Search Report and Written Opinion dated Jan. 3, 2014, which issued in corresponding International Application No. PCT/US2013/049596.
Lal, S. et al., "Antibiotic therapy for Crohn's disease: A review," Can J. Gastroenterol, vol. 20, No. 10, pp. 651-655 (2006).
Lee et al., "Pneumocystis Jiroveci Pneumonia and Pneumomediastinum in an Anti-TNFalpha Naive Patient with Ulcerative Collitis," World Journal of Gastroenterology, vol. 15, No. 15, pp. 1897-1900 (2009).
Rizzello F. et al.: "Prophylaxis of postoperative recurrence of Crohn's disease: Combination of antibiotic and probiotic versus mesalamine", Digestive and Liver Disease Supplements; International Meeting on Inflammatory Bowel Diseases; Capri, Italy; Jun. 18-21, 2000, vol. 32, no. supplement 1, pp. A37 (2000).

(Continued)

*Primary Examiner* — Tracy Vivlemore
*Assistant Examiner* — Monica Shin
(74) *Attorney, Agent, or Firm* — Jonathan D. Ball; Greenberg Traurig

(57) ABSTRACT

Methods and compositions for treating inflammatory bowel disease involve the use of targeted antibiotics in combination with probiotic formulations. The probiotics mitigate many of the deleterious side effects associated with antibiotic use and permit the antibiotic to be administered at a higher dose and for a longer duration than would otherwise be possible in the absence of the probiotic. The practice of the invention may reduce or eliminate the use of immunosuppressants in the treatment and management of IBD.

18 Claims, No Drawings

(56) References Cited

OTHER PUBLICATIONS

Savidge R S.: "Trimethoprim and sulphamethoxazole in ulcerative colitis", Postgraduate Medical Journal, vol. 45 (1969).
Sheil B. et al., "Probiotic Effects on Inflammatory Bowel Disease," J. Nutr., vol. 137, pp. 819S-824S (2007).
Supplemental European Search Report completed Sep. 5, 2013, which issued in corresponding EP application No. 10841670.
University of Maryland Medical Center, "Crohn's disease," <http://umm.edu/Health/Medical/Ency/Articles/Crohns-disease>, pp. 1-7 (2013).
University of Maryland Medical Center, "Ulcerative colitis," <http://umm.edu/health/medical/ency/articles/ulcerative-colitis>, pp. 1-6 (2013).

* cited by examiner

COMPOSITIONS AND METHOD FOR TREATMENT AND PROPHYLAXIS OF INFLAMMATORY BOWEL DISEASE

This application is a continuation application of U.S. Ser. No. 13/517,486, filed Jun. 20, 2012, which is a National Phase application of International Application No. PCT/US2010/062339, filed Dec. 29, 2010, which claims priority under 35 U.S.C. 119(e) to U.S. Provisional Application No. 61/291,474, filed Dec. 31, 2009. The entirety of each application is incorporated by reference herein for all purposes.

FIELD OF INVENTION

The present invention relates generally to compositions and methods for the prophylaxis and treatment of inflammatory bowel disease (IBD) due to bacterial infection. More specifically, this invention envisions the use of probiotic formulations in combination with antibiotics to treat IBD symptoms and to reduce the risk of relapse.

BACKGROUND

Inflammatory bowel disease (IBD) is a group of inflammatory conditions of the colon and small intestine that affect over two million people in the United States and an estimated eight million people worldwide. The two phenotypes of IBD most commonly referred to are Crohn's disease (CD) and ulcerative colitis (UC). CD commonly manifests as inflammation of the small intestine, but can affect other parts of the body as well. UC is usually characterized by inflammation of the mucosa of the colon and rectum. Symptoms of IBD most commonly include fever, vomiting, diarrhea, bloody stool (hematochezia), abdominal pain, and weight loss, but also may include a host of other problems. The severity of symptoms may impair the quality of life of patients that suffer from IBD.

Although the etiology of IBD is poorly understood, many theories have been proposed. UC and CD are commonly regarded as autoimmune diseases, with evidence suggesting they are the result of a misdirected immune response. The etiology of IBD appears to involve complex interactions of genetic predisposition, environmental factors, disruption of the intestinal microbiome, and an overly aggressive immune response. In addition, evidence linking the ability of intestinal epithelial cells to modify the mucosal immune response, may suggest an invasive bacterial pathway. The integrity of the gut epithelial barrier is critical in influencing progression to disease. Imbalance in intestinal microbiota of gut friendly bacteria destroyed by antibiotics as well as opportunistic pathogens are implicating factors as well. Additional factors influencing activation may include the unfolded protein response (a result of cellular stress), toll like receptors, invasive bacteria, TNF factors, DNA/RNA genetic mutations effecting encoding proteins IL-10R1-IL10R2, spontaneous mutation of normal gut bacteria, uncontrolled T-cell activation, and enteroinvasive and adherent invasive strains of *E. coli* bacteria. Disruption in the gut epithelial barrier when bacterial overgrowth overwhelms the body's defense mechanism to cope, the immune/inflammatory response, if left unchecked, often results in chronic inflammation, a precursor to full blown disease. The involvement of luminal bacteria as a cause of chronic inflammation and disease is well documented. See, e.g., Kucharzik et al., "Recent understanding of IBD pathogenesis: implications for future therapies," *Inflamm. Bowel Dis.*, 2006 November; 12(11):1068-83. Genetic studies have implicated IL12B and NOD2 in increased susceptibility to Mycobacterial disease, and suggest that this combination of genetics and bacterial infection are implicating factors in Crohn's disease as well as ulcerative colitis. The possibility therefore exists as to *Mycobacterium* infection being among the several microbial triggers in IBD.

Patients with IBD have been reported to house an abnormal microbiota. Whether this altered flora is the cause or the result of chronic inflammation remains unclear. As yet, questions remain whether commensal enteric bacteria or invasive strains of pathogenic bacteria, particularly *Escherichia coli*, are a direct trigger cause in IBD. Both may be contributing factors in different subsets of patients.

Involvement of intestinal microflora in the pathogenesis of IBD has been suggested but trials on the use of antibiotic treatment in patients with UC have produced contrasting results. See, for example, M. Guslandi, "Antibiotics for inflammatory bowel disease: do they work?"*Eur. J. Gastroenterol. Hepatol.*, 2005 February; 17(2):145-7; Gionchetti et al., "Review—antibiotic treatment in inflammatory bowel disease: rifaximin, a new possible approach," *Eur. Rev. Med. Pharmacol. Sci.*, 1999 January-February; 3(1):27-30. However, the weight of evidence supports the use of antibiotics such as metronidazole, ciprofloxacin, or rifaximin in the treatment of IBD. See, Rubin, D. T., et al., "Role of antibiotics in the management of inflammatory bowel disease: a review," *Rev. Gastroenterol. Disord.*, 2005; 5 Suppl. 3:S10-5. Studies by J. T. Danzi and others demonstrate the effectiveness of adjuvant use of sulfamethoxazole-trimethoprin in patients with CD and UC in terms of steroid withdrawal and maintenance of remission. See Danzi, J. T. "Trimethoprim-Sulfamethoxazole Therapy of Inflammatory Bowel Disease," *Gastroentemology*, Vol. 96, No. 5, Part 2, p. A110. However, the use of sulfamethoxazole-trimethoprin as a first-line therapy, rather than as an adjuvant to immunosuppressant therapy, is not suggested.

One complication associated with the use of broad-spectrum antibiotics is the depletion of beneficial microflora in the gut, leading to opportunistic infection by competing bacteria in the intestine, including *Clostridium difficile*. *C. difficile* infection can limit the duration of antibiotic therapy and can lead to pseudomembranous colitis, which may compound the symptoms of IBD. See Trnka, Y. M., et al., "Association of *Clostridium difficile* toxin with symptomatic relapse of chronic inflammatory bowel disease," Gastroenterology, 1981 April; 80(4):693-6; Freeman, H. J., "Recent developments on the role of *Clostridium difficile* in inflammatory bowel disease," *World J. Gastroenterol.*, 2008 May 14; 14(18):2794-6. In fact, it has been suggested that the frequent use of broad spectrum antibiotics in treating IBD could exacerbate symptoms and prevent remission of UC symptoms. See Miner, J. et al., "Steroid-refractory ulcerative colitis treated with corticosteroids, metronidazole and vancomycin: a case report," *BMC Gastroenterol.*, 2005; 5:3. Many antibiotics currently used have been ineffective in achieving sustained control of remission in part due to dosage and duration.

Probiotics are live microbial organisms that beneficially affect the microbiome of the host and treatment of various disorders of the gastrointestinal tract, including IBD, using probiotics is well-known. See, e.g., Schultz M., et al, "Rationale for probiotic treatment strategies in inflammatory bowel disease," *Expert Rev. Gastroenterol. Hepatol.*, 2008 June; 2(3):337-55. For example, treatment of IBD using specific probiotic *E. coli* strains is disclosed in U.S. Pat. No. 7,018, 629, to Jacob et al. Likewise, prophylaxis and treatment of IBD with an endogenous strain of *Bifidobacterium* is described in U.S. Patent Pub. No. 2002/0006432, to Collins et al. However, probiotics alone will not cure IBD, nor will they be a direct cause of remission.

The combination of probiotics and antibiotics has been proposed. For example, U.S. Pat. No. 6,461,607 to S. Farmer describes therapeutic compositions for the treatment of a gastrointestinal infection caused by pathogenic bacteria, comprising antibiotic-resistant lactic-acid producing bacteria and an antibiotic, although no mention is made of the treatment of IBD.

There clearly is a continuing need for new therapies in the treatment and control of IBD. It is therefore an object of this invention to provide compositions and methods for an alternative treatment option for IBD.

SUMMARY OF INVENTION

The invention is premised on the theory that IBD may result from an overactive immune response to invasive or commensal pathogenic bacterial infection in the gastrointestinal tract. Therefore, in IBD cases where pathogenic bacterial infection is suspected, it may be possible to achieve clinical remission of symptoms and prevent relapse with high-dose antibiotics administered for a duration of time sufficient to completely eradicate the bacterial antigen and its spores, allowing for restoration of the gut epithelial barrier. The invention also envisions the use of high-dose, selective probiotics to counter the deleterious effects of antibiotic therapy on the natural enteric microflora and promote healing of the mucosa and intestinal epithelial barrier by restoring and maintaining the natural enteric microflora.

In one aspect of the invention, therapeutic compositions are provided comprising antibiotics and probiotics. The antibiotics and probiotics may be combined in a unitary dosage form to improve patient compliance with the treatment protocols. Accordingly, one aspect of the invention relates to a multi-layer tablet for the treatment or prophylaxis of inflammatory bowel disease due to pathogenic bacterial infection. The multi-layer tablets comprises:

(i) a delayed-release layer comprising an amount of antibiotic effective to reduce colonization of pathogenic bacteria in the gastrointestinal tract, preferably a combination of:

sulfamethoxazole, and trimethoprim; and (ii) an immediate-release layer comprising a probiotic formulation in an amount effective to restore normal microflora colonies in the gut, preferably including at least one strain selected from:

Bifidobacterium bifidum;
Bifidobacterium breve;
Bifidobacterium infantis;
Bifidobacterium longum;
Lactobacillus acidophilus;
Lactobacillus bulgaricus;
Lactobacillus paracasein;
Saccharomyces boulardii, and combinations thereof.

The immediate-release layer preferably surrounds the delayed-release layer and releases the probiotic formulation upon contact with gastric fluid in the stomach. The delayed-release layer preferably comprises an enteric coating of a polymer which releases the antibiotic primarily in the terminal ileum.

In another aspect of the invention, a method for treatment or prophylaxis of inflammatory bowel disease due to bacterial infection is provided. The method is based on the principle that achieving and maintaining remission requires high doses of targeted antibiotics and a duration of treatment sufficient to completely eradicate the offending bacterial antigens and their components. Therefore, the method of the invention may comprise daily administration for extended durations, preferably for a period of at least 120 days, of a composition comprising:

(i) an amount of antibiotic effective to reduce colonization of pathogenic bacteria in the gastrointestinal tract, the antibiotic preferably comprising a combination of sulfamethoxazole and trimethoprim, and (ii) a probiotic formulation in an amount effective to restore normal microflora colonies in the gut, the probiotic formulation preferably including at least one strain selected from those listed above.

The daily dosage of both antibiotic and probiotic will typically be higher during the treatment of active symptoms than during the maintenance or prophylaxis stage of therapy. For example, a preferred therapeutic regimen comprises, in sequential steps:

(a) a first step for the treatment of active symptoms comprising twice daily administration of about 800 mg of sulfamethoxazole, about 160 mg of trimethoprim, and at least about 20 billion cells of probiotics (for a total daily dose of about 1,600 mg of sulfamethoxazole, about 320 mg of trimethoprim, and at least about 40 billion cells of probiotics), for a period from 120 to 180 days, and (b) a second step for prophylactic treatment after clinical remission of symptoms comprising once daily administration of about 800 mg of sulfamethoxazole, about 160 mg of trimethoprim, and at least about 20 billion cells of probiotics, for a period from 120 to 180 days.

While ulcerative colitis rarely remits completely, the risk of relapse can be greatly reduced with continued proactive treatment according to the invention, and thus the protocols of the invention provide a new direction for the treatment of inflammatory bowel disease. The invention may achieve and maintain remission without incurring the significant toxic side-effects related to steroids and immunosuppressants, and for many patients suffering from chronic inflammation, the invention may mitigate the prospect for colorectal surgery.

These and other aspects of the invention will be better understood by reading of the following detailed description and appended claims.

DETAILED DESCRIPTION

The role of pharmabiotics in the treatment of IBD is well-documented. The present invention envisions the treatment or prophylaxis of inflammatory bowel disease, including ulcerative colitis (UC) and Crohn's disease (CD), using antibiotics in combination with probiotics. The invention is based on early intervention with targeted antibiotics through control of dosage and duration of treatment, to eradicate invasive or commensal bacterial infection which may allow for restoration of the gut epithelial barrier, with the help of selective probiotics. It is postulated that the immune response may "reset" once the offending antigen is completely eradicated and the immune system is unburdened by toxic immunosuppressants, thus leading to an improved prognosis.

The method of the invention entails treatment of individuals suffering from UC, CD, or any other form of IBD. The UC or CD may be in the active stage or in remission during treatment. In one embodiment, the treatment is targeted to a patient for whom a clinical diagnosis of IBD, and in particular UC or CD, has been made. The patient may be a male, female, adult, geriatric or pediatric patient. Veterinary use, particularly for mammals, is also contemplated.

The invention provides a treatment regimen which involves daily administration of antibiotics and probiotics to a patient in need thereof. The administration is preferably oral, but other routes are also contemplated, including for example, rectal administration. Where the patient is in the active stage of disease, the treatment is carried out daily for a period of time sufficient to resolve one or more of the symptoms of IBD, which typically will be at least 120 days, preferably at least 150 days, and more preferred still at least 180 days. Once the IBD symptoms abate, the treatment is preferably carried out for an additional period of time to kill any remaining latent spores in the intestines. This additional treatment will typically comprise daily administration, albeit with a fraction of the initial dose, for example, half of the therapeutic dose used in the initial treatment regimen, and typically will be for at least 120 days, preferably at least 150 days, and more preferred still at least 180 days. The goal of the follow-on treatment is to reduce the risk of relapse.

In the initial treatment stage, when the disease is active, it is preferred to give an oral dose twice daily (B.I.D.). However, once daily, as well as more frequent administration, is contemplated. The dosages can be taken, for example, in the morning and before bed, and can be taken with or without a meal. In the maintenance stage, i.e., after a flare-up has resolved, once daily dosing is contemplated, although more or less frequent administration is likewise within the scope of the invention.

The treatment regimen comprises administration, preferably oral administration, of an antibiotic drug and a probiotic formulation, in amounts effective to reduce colonization of invasive bacteria, such as adherent-invasive *Escherichia coli* (AIEC) and/or enteroinvasive *Escherichia coli* (EIEC), *Salmonella*, and various strains of *Shigella* in the gastrointestinal tract. Without wishing to be bound to any particular theory, it is believe that bacterial infection may be a trigger cause of inflammation in IBD. This theory finds support in the observation that biopsies of inflamed tissue show high levels of invasive strains of *E. Coli* and the number of bacteria in the inflamed region correlates with the severity of bowel inflammation, as well as the fact that animals raised in germ-free environments do not develop colitis. Also, the linkage of *Mycobacterium paratuberculosis* to UC and CD is highly suggestive in T-cell activation, implicating this bacterium in the etiology of IBD.

This invention counteracts the action of antibiotics in destroying healthy colonies of microflora in the gut and mitigates the risk of developing opportunistic infection by competing bacteria in the intestine, including *Clostridium difficile*. Consequently, it is believed that the inventive combination permits a higher dose of antibiotic to be employed for a longer duration than would be possible in the absence of the probiotic mixture. In this manner, not only is it possible to resolve symptoms of IBD, but the treatment allows for the eradication of latent spores, thereby reducing the probability of relapse.

In the broadest sense of the invention, any antibiotic drug having activity against invasive bacterial infections of the intestines is contemplated to be useful. The antibiotic component may have bactericidal and/or bacteriostatic activity against the invasive species. Preferred antibiotics will have an activity against at least one bacteria selected from the group consisting of *Escherichia coli* (*E. coli*), enterotoxigenic strains of *E. coli* (ETEC) that cause bacterial gastroenteritis, indole-positive *Proteus* species, *Proteus mirabilis*, *Proteus vulgaris*, *Morganella morganii*, *Klebsiella* species, *Enterobacter* species, *Haemophilus influenzae*, *Streptococcus pneumoniae*, *Shigella flexneri*, or *Shigella sonnei*. However, antibiotics having activity against *E. Coli*, and in particular invasive strains of *E. Coli* are favored. Preferably, the antibiotic component is active against enterotoxigenic strains of *E. coli*, adherent-invasive *E. coli* (AIEC) and/or enteroinvasive *E. coli* (EIEC) in the gastrointestinal tract.

The mechanism of action of the antibiotic drug is not important, provided that it is effective in reducing infection of invasive species in the intestines. However, in one embodiment, it has been found useful to employ an antibiotic that inhibits folate synthesis in bacteria. This pathway involves a multi-step synthesis for the production of tetrahydrofolic acid, an essential coenzyme in many biologic reactions, particularly those relating to the synthesis of amino acids and nucleic acids. Useful antibiotic may act on any stage in the bacterial folate synthesis pathway, and may inhibit the bacterial synthesis of one or more intermediates of the tetrahydrofolic synthesis pathway, such as dihydrofolic acid.

In one embodiment, the antibiotic component comprises a drug which inhibits a first step of the tetrahydrofolic synthesis pathway involving the synthesis of dihydropteroic acid from dihydropteroate diphosphate and para-aminobenzoic acid (PABA), catalyzed by the enzyme dihydropteroate synthetase. Specifically, the antibiotic drug may act as a false-substrate inhibitor of dihydropteroate synthetase and compete with PABA for binding to dihydropteroate synthetase. Suitable antibiotics therefore include drugs that are competitive inhibitors of bacterial dihydropteroate synthetase, including para-aminobenzoic acid (PABA) analogs.

On such class of drugs are the antibacterial sulfonamides, namely 4-amino-N-(5-methyl-3-isoxazolyl)benzenesulfonamide, which has the generic name sulfamethoxazole. Sulfamethoxazole has the molecular formula of $C_{10}H_{11}N_3O_3S$, and the following structure:

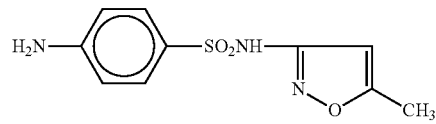

The antibiotic component may also comprise a drug that inhibits the last step in the tetrahydrofolic acid synthesis pathway in bacteria, which involves the conversion of dihydrofolic acid to tetrahydrofolic acid with the enzyme dihydrofolate reductase. In particular, the antibiotic drug may inhibit the synthesis of tetrahydrofolic acid by, for example, inhibiting the activity of dihydrofolate reductase. A suitable compound for inhibiting dihydrofolate reductase is 5-[(3,4,5-trimethoxyphenyl)methyl]-2,4-pyrimidinediamine, which has the generic name trimethoprim, the molecular formula of $C_4H_{18}N_4O_3$, and the structure:

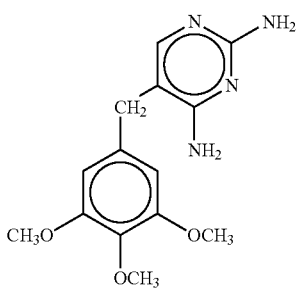

In a preferred embodiment, the antibiotic component may comprise at least two drugs that affect distinct steps in the bacterial biosynthesis of tetrahydrofolate. Preferred is a combination of a drug that competitively inhibits the activity dihydropteroate synthetase with a drug that inhibits dihydrofolate reductase in bacteria. In particular, the antibiotic component may include a combination of trimethoprim and sulfamethoxazole.

In certain embodiments, the antibiotic component may comprise a combination of trimethoprim and sulfamethoxazole in a weight ratio from about 1:2 to about 1:50, preferably from about 1:3 to about 1:30, more preferably from about 1:4 to about 1:25, even more preferred still from about 1:5 to about 1:20. In a specific embodiment, the antibiotic component may comprise a combination of trimethoprim and sulfamethoxazole in a ratio of 1:5.

In some embodiments, the antibiotic component may comprise from about 40 mg to about 320 mg of trimethoprim, more typically from about 80 mg to about 160 mg of trimethoprim. In certain embodiments, the antibiotic component may comprise about 40 mg, 50 mg, 60 mg, 70 mg, 80 mg, 90 mg, 100 mg, 110 mg, 120 mg, 130 mg, 140 mg, 150 mg, or about 160 mg of trimethoprim. In some embodiments, the antibiotic component may comprise from about 200 mg to about 1,600 mg of sulfamethoxazole, more typically from about 400 mg to about 800 mg of sulfamethoxazole. In certain embodiments, the antibiotic component may comprise about 200 mg, 250 mg, 300 mg, 350 mg, 400 mg, 450 mg, 500 mg, 550 mg, 600 mg, 650 mg, 700 mg, 750 mg, or about 800 mg of sulfamethoxazole. In one embodiment, the antibiotic component comprises 80 mg of trimethoprim in combination with 400 mg of sulfamethoxazole. In another embodiment, the antibiotic component comprises 160 mg of trimethoprim in combination with 800 mg of sulfamethoxazole.

Other antibiotic drugs which may be used include, without limitation, vancomycin; amoxicillin; tetracyclines; clarithromycin; clindamycin; a member of the cephlosporin antibiotic family (e.g., cefaclor, cefadroxil, cefixime, cefprozil, ceftriaxone, cefuroxime, cephalexin, loracarbef, and the like); a member of the penicillin family of antibiotics (e.g., ampicillin, amoxicillin/clavulanate, bacampicillin, cloxicillin, penicillin VK, and the like); a member of the fluoroquinolone family of antibiotics (e.g., ciprofloxacin, grepafloxacin, levofloxacin, lomefloxacin, norfloxacin, ofloxacin, sparfloxacin, trovafloxacin, and the like); or a member of the macrolide antibiotic family (e.g. azithromycin, crythromycin, and the like). Specific mention may be made of the following preferred antibiotics, and in particular at the dosages indicated: levofloxacin (e.g., 250 mg, 500 mg, or 750 mg), metronidazole (e.g., 250 mg, 500 mg, or 750 mg), ciprofloxacin (e.g., 100 mg, 250 mg, 500 mg, or 750 mg), amoxicillin (e.g., 125 mg, 200 mg, 250 mg, 400 mg, 500 mg, 600 mg, 775 mg, or 875 mg), erythromycin (e.g., 250 mg, 333 mg, or 500 mg), vancomycin (e.g., 125 mg or 250 mg), and clindamycin (e.g., 75 mg, 150 mg, or 300 mg), each of which may be used alone or in combination with other antibiotics. Each of the forgoing dosages may be administered up to the maximum safe daily dosage for each given drug. The may constitute, for example, administration of one, two, three, four, or more of the foregoing doses daily. In one embodiment, the treatment comprises oral administration of trimethoprim and sulfamethoxazole, optionally in combination with at least one other antibiotic drug selected from the group consisting of levofloxacin, metronidazole, ciprofloxacin, amoxicillin, crythromycin, vancomycin, clindamycin, and combinations thereof.

The second component of the compositions and treatment methods according to the invention is a probiotic formulation. The digestive systems of humans and other mammals include bacteria essential to the health of the gastrointestinal system and overall heath of the individual. Beneficial types of bacteria, such as lactic acid bacteria, provide various health benefits, including enhancing digestion, nutrient absorption, bowel function, and natural immunity. Also, beneficial bacteria may produce vitamins and, moreover, may inhibit the growth of pathogenic microorganisms, such as pathogenic bacteria, viruses, and/or protozoa. Beneficial bacteria may inhibit the growth of such undesirable microorganisms, for example, by secreting bacteriocins and/or substances that reduce gastrointestinal tract pH, thereby making the gastrointestinal environment less hospitable to pathogenic microorganisms. Disruption of the balance of the normal intestinal flora can lead to conditions ranging from mild gastrointestinal symptoms to serious infection.

Examples of probiotics useful in the present invention include, without limitation, bacteria selected from the group consisting of *Bifidobacterium, Lactobacillus, Streptococcus, Propionibacterium*, and *Enterococcus*, and mixture thereof. Particular non-limiting examples of probiotics include *Arthrobacter agilis, Arthrobacter citreus, Arthrobacter globiformis, Arthrobacter leuteus. Arthrobacter simplex, Azotobacter chroococcum, Azotobacter paspali, Azospirillum brasiliencise, Azospriliium lipoferum, Bacillus brevis, Bacillus macerans, Bacillus pumilus, Bacillus polymyxa, Bacillus subtilis, Bacteroides lipolyticum, Bacteroides succinogenes, Brevibacterium lipolyticum, Brevibacterium stationis, Bacillus laterosporus, Bacillus bifidum, Bacillus laterosporus, Bifidophilus infantis, Streptococcus thermophilous, Bifidophilus longum, Bifidobacteria animalis, Bifidobacteria bifidus, Bifidobacteria breve, Bifidobacteria longum, Kurtha zopfil, Lactobacillus paracasein, Lactobacillus acidophilus, Lactobacillus planetarium, Lactobacillus salivarius, Lactobacillus rueteri, Lactobacillus bulgaricus, Lactobacillus helveticus, Lactobacillus casei, Lactobacillus rhamnosus. Lactobacillus sporogenes, Lactococcus lactis, Myrothecium verrucaris, Pseudomonas calcis, Pseudomonas dentrificans. Pseudomonas flourescens, Pseudomonas glathei, Phanerochaete chrysosporium, Saccharomyces boulardii, Streptmyces fradiae, Streptomyces cellulosae, Stretpomyces griseoflavus*, and combinations thereof.

Special mention may be made of lactic acid bacteria (LAB) and *bifidobacteria*. In some embodiments, the probiotic component comprises cells or spores of at least one strain selected from the group consisting of *Bifidobacterium bifidum, Bifidobacterium breve, Bifidobacterium longum, Saccharomyces boulardii, Lactobacillus acidophilus, Lactobacillus bulgaricus, Lactobacillus paracasein*, and combinations thereof. Commercially available probiotic formulations include Culturelle® from Amerifit Brands, Inc., which contains *Lactobacillus* GG, and VSL#3® from VSL Pharmaceuticals, Inc. which contains *Lactobacillus* and *Bifidobacterium* and is positioned for the treatment of IBD.

In one embodiment, the probiotic mixture comprises *Bifidobacterium bifidum*. In one embodiment, the probiotic mixture comprises *Bifidobacterium breve*. In one embodiment, the probiotic mixture comprises *Bifidobacterium longum*. In one embodiment, the probiotic mixture comprises *Saccharomyces boulardii*. In one embodiment, the probiotic mixture comprises *Lactobacillus acidophilus*. In one embodiment, the probiotic mixture comprises *Lactobacillus bulgaricus*. In one embodiment, the probiotic mixture comprises *Lactobacillus paracasein*.

In some embodiments, the dose is from about $1 \times 10^3$ to about $1 \times 10^{12}$ colony forming units (cfu) of probiotic, from about $1 \times 10^5$ to about $1 \times 10^{12}$ cfu of probiotic, or from about $1 \times 10^7$ to about $1 \times 10^{12}$ cfu of probiotic, per day. The probiotic mixture will typically comprise at least 500 million cells or spores, more typically at least 1 billion, preferably at least 5 billion, more preferably at least 10 billion, and more preferred still at least 20 billion cells or spores. During the treatment regimen, where the dosing is twice daily, up to 40 billion cells or spores or even more will be ingested daily.

In certain embodiments, a purified, isolated, and/or genetically altered bacterial strain can be used. For example, a strain can be genetically altered in a number of different ways to increase efficacy. Exemplary methods are described in Methods in Cloning Vol. 3, eds. Sambrook and Russell, Cold Spring Harbor Laboratory Press (2001) and references cited therein. In addition, probiotic bacteria of the present invention can be obtained commercially. A variety of beneficial bacteria are commercially available from American Type Culture Collection Catalogue (Rockville, Md.). Beneficial bacteria can also be obtained by culturing, for example, in liquid, or on solid media, following routine and established protocols, and isolated from the medium by conventional means. Exemplary methods are described in Methods in Cloning Vol. 3, eds. Sambrook and Russell, Cold Spring Harbor Laboratory Press (2001) and references cited therein.

Additional examples of probiotics include strains of *Bifidobacterium* isolated from the human gastrointestinal tract, e.g., see WO 00/42168; strains of *Bifidobacterium infantis* disclosed in U.S. Pat. No. 7,195,906; and other bacterial and microbe strains disclosed in U.S. Patent Pub. No. 2008/0241226, the contents of each of which are herein incorporated by reference in their entireties.

In some embodiments, the probiotic is dried. Drying may comprise spray drying, fluid bed drying, or freeze-drying. In some embodiments, for example, a cell suspension is treated with proteins, maltodextrins, trehalose, and optionally, other stabilizing or freeze-protecting agents like ascorbic acid, to form a viscous paste, which is submitted to freeze-drying. The so-obtained material can be grinded to appropriate size in suitable dosage forms.

What is important is that the probiotic formulation provide a sufficient number of cells to substantially maintain levels of microflora in the gastrointestinal tract during the course of treatment. The levels of microflora in the gastrointestinal tract at the end of the treatment regimen may be, for example, greater than the levels that would otherwise be present at the end of the course of treatment were the probiotic mixture not administered. The methods are also useful for reducing the risk of *C. difficile* infection during antibiotic treatment of IBD.

The use of probiotics may have ancillary benefits including treatment of abdominal cramps, abdominal discomfort, abdominal distension, antibiotic associated diarrhea (AAD), belching, bloating, celiac disease, cholecystitis, *Clostridium difficile* associated diarrhea (CDAD), Crohn's disease, constipation (including chronic or functional constipation), diarrhea (including chronic or functional diarrhea), disorders of motility, diverticulitis or diverticular disease, duodenal ulcers, dyspepsia (including functional dyspepsia), erosive esophagitis, excess flatus, gall bladder disease, gastroesophageal reflux disease (GERD), gastroparesis, gastritis, gastric ulcers, halitosis, heartburn, hypersecretory conditions such as Zollinger-Ellison syndrome, inflammatory bowel disease (IBD), irritable bowel syndrome (IBS), lactose intolerance, motion sickness, multiple endocrine adenomas, nausea, pain, posterior laryngitis, post-infection colitis, pouchitis, small intestine bacterial overgrowth (SIBO) or small bowel bacterial overgrowth (SBBO), spasm, spastic colon, stomach problems, systemic mastocytosis, ulcerative colitis (UC), visceral hypersensitivity, vomiting, and the like.

The treatment methods are contemplated to be useful for the treatment, prevention, amelioration, or reduction of symptoms of inflammatory bowel disease. Also provided, are methods for the treatment or prophylaxis of ulcerative colitis (UC) and/or Crohn's disease (CD). The method will find utility in the treatment of UC in either the active stage or during remission to prevent or reduce the probability or occurrence of relapse.

In severe cases of IBD, conventional treatment relies on suppression or modulation of the immune system. Immunosuppressants including azathioprine, methotrexate, and 6-mercaptopurine have been suggested in the treatment of IBD. However, the use of immunosuppressants is controversial because they do not address the underlying cause of illness and their severe side-effects may outweigh their benefits. Indeed, it has been suggested by researchers at University College London, who question the wisdom of suppressing the immune system in CD and UC patients, that the problem may be an underactive, rather than an overactive immune system. Therefore, in the preferred practice of the present invention, the patient is not administered an immunosuppressant or immunomodulatory drug during the treatment regimen, or if the patient had been on immunosuppressant or immunomodulatory drugs prior to starting the treatment, the levels of immunosuppressant or immunomodulatory drugs are preferably reduced or substantially eliminated during treatment. In some embodiments, the patient is not administered azathioprine, methotrexate, or 6-mercaptopurine during the treatment regimen or the levels of these drugs are reduced. In another embodiment, the patient is not administered a TNF-α inhibitor during the treatment regimen. The diminished use of immunosuppressants may result in unhindered DNA/RNA repair mechanisms.

While not strictly necessary, it may be beneficial to include daily administration of an aminosalicylate, such as mesalamine (5-aminosalicylic acid), in conjunction with the treatment protocol. Mesalamine is marketed in the United States under the names Asacol and Lialda. Mesalamine is preferably administered in an mount from about 3.6 g to about 4.8 g daily. In one embodiment, 9-12 tablets of 400 mg of Asacol (mesalamine) are given daily. In another embodiment, 3-4 tablets of 1.2 g of Lialda (mesalamine) are given daily. However, in some embodiment, the patient is not treated with aminosalicylates.

It has also been found useful to administer fish oil or other sources of omega-3 fatty acids including eicosapentaenoic acid (EPA) and docosahexaenoic acid (DHA). In one embodiment, at least 1,000 mg of omega-3 fatty acids daily are taken daily, and more preferably twice daily. Other dietary measures are recommended in concert with the treatment regimen, including for example, limiting alcohol and refined sugars, limiting or eliminating gluten, wheat, whey, red meat and dairy products, and limiting fat intake. It also may be desirable to limit or eliminate folic acid and/or iron supplements.

Once the primary symptoms of IBD have subsided, the dosage of antibiotic can be reduced, and may be cut in half. It is important to continue the therapy, however, to eradicate any latent spores of invasive bacteria. Failure to totally eradicate the offending bacterial pathogen along with lingering spores may contribute to perpetuating a state of chronic inflammation and, consequently, lessen the possibility of remission. Once full clinical remission is noted, the treatment regimen is stopped, but it may be desirable to continue to administer probiotics daily in order to maintain the microflora in the gut and inhibit colonization of invasive species.

Preferred methods for the treatment or prophylaxis of inflammatory bowel disease comprise daily oral administration to a patient in need thereof for a period of at least 120 days (preferably for 180 days) a dose of about 1.600 mg daily of sulfamethoxazole, 320 mg daily of trimethoprim, and a probiotic mixture comprising at least about 40 billion cells. The probiotic will preferably comprise at least one strain selected from the group consisting of *Bifidobacterium bifidum*, *Bifidobacterium breve*, *Bifidobacterium Infantis*, *Bifidobacterium longum*, *Saccharomyces boulardii*, *Lactobacillus acidophilus*, *Lactobacillus bulgaricus*, *Lactobacillus paracasein*, and combinations thereof.

In one variant, the patient is administered 800 mg of sulfamethoxazole twice daily and 160 mg of trimethoprim twice daily for a time sufficient to affect remission of one or more symptoms of inflammatory bowel disease, after which the patient is administered 800 mg of sulfamethoxazole once daily and 160 mg of trimethoprim once daily for a period of at least 90-120 days after the onset of remission. The dosing also may be based on the patient's weight. For example, adult patients weighing up to 175 pounds, or up to 190 pounds, may be administered two tablets daily, whereas patients over 190 pounds may be administered 2½ tablets daily, each tablet comprising 800 mg of sulfamethoxazole and 160 mg of trimethoprim.

This invention has the potential to prevent pathogenic microorganisms from upsetting the balance of normal gut flora and destabilizing the gastrointestinal tract, while eradicating the invasive pathogen. The results of treatment may include (1) disruption of the cycle of chronic inflammation allowing for restoration of the gut epithelial barrier; (2) preventing or minimizing translocation of intestinal bacterial to other organs; (3) reversing or preventing side effects of antibiotic therapy; (4) minimizing a causal effect leading to *C. Difficile* via antibiotics; (5) eradicating pathogenic bacteria strains along with its components; (6) produce quality, long-term remission, (7) recolonize and maintain the balance of intestinal flora; (8) disrupt the chain of events leading to the immune/inflammatory response, cellular changes, and chronic inflammation; (9) allow for increased absorption; (10) modulate transcription of Tumor Necorsis Factor-A (TNF-α); (11) possibly mitigate the risk of colorectal cancer due to chronic inflammation; and (12) achieve and maintain remission without incurring the significant toxic side effects related to steroids and immunosuppressants.

In one embodiment, the sulfamethoxazole, trimethoprim, and probiotic mixture are present in a single dosage form, although it is also possible that the sulfamethoxazole and said trimethoprim are included in a first dosage form and the probiotic mixture is present in a second dosage form. When the antibiotics and the probiotics are included in separate dosage forms, it is preferred, but not strictly necessary, that they be administered substantially simultaneously.

The oral dosage form will typically comprise at least about 1 billion cells of probiotics, at least about 2 billion cells of probiotics, at least about 5 billion cells of probiotics, at least about 10 billion cells of probiotics, or at least about 20 billion cells of probiotics, based on the collective number of cells of all species and strains.

In embodiments in which the dosage form comprises about 800 mg of sulfamethoxazole and about 160 mg of trimethoprim, at least about 20 billion cells of probiotic will be included. For example, the dosage form may comprise:
  about 5 billion cells of *Bifidobacterium bifidum;*
  about 2 billion cells of *Bifidobacterium breve;*
  about 2 billion cells of *Bifidobacterium infantis;*
  about 2 billion cells of *Bifidobacterium longum;*
  about 5 billion cells of *Lactobacillus acidophilus;*
  about 500 million cells of *Lactobacillus bulgaricus;*
  about 2 billion cells of *Lactobacillus paracasein;* and
  about 2.5 billion cells of *Saccharomyces* boulardii.

In embodiments in which the dosage form comprises about 400 mg of sulfamethoxazole and about 80 mg of trimethoprim, at least about 10 billion cells of probiotic will be included. In this "half-strength" formulation, the dosage form may include half the amount of cells listed above for each species. In embodiments in which the dosage form comprises about 200 mg of sulfamethoxazole and about 40 mg of trimethoprim, at least about 5 billion cells of probiotic will be included, in which case the dosage form may include one quarter of the amount of cells listed above for each species.

Those of skill in the art will appreciate that microorganisms that are intended to act in the intestinal tract should be protected against the acidic gastric juice of the stomach. Preferred dosage forms include an enteric tablet, capsule, powder or granulate that will survive the stomach and arrive intact in the intestine. Further, embedded microorganisms in a carrier or protective matrix may tend to cake due to hygroscopicity, impeding flowability and reducing storage stability. Techniques for achieving low hygroscopicity and good flowability in tablets, capsules, and the like, and especially in powdered products involving microorganisms, are described, e.g., in U.S. Patent Pub. No. 2009/0214647, which is incorporated herein by reference in its entirety.

The oral dosage form may comprise tablets, capsules, powders or sachets, but will typically be in the form a tablet. The tablet can be a modified-release tablet, including sustained release and delayed release. The dosage form can be designed according to any of the modified release dosage forms known in the art and described, for example, in U.S. Pat. No. 7,108,865, the disclosure of which is hereby incorporated by reference, and using any of the carriers, coatings, excipients, and tablet designs in the patent.

In some embodiments, the antibiotic and probiotic components are compressed with a binder together into a solid core. In one embodiment, the probiotic component is in a solid core and the antibiotic is contained in a layer surrounding the core. In another embodiment, the antibiotic component is in a solid core and the probiotic is contained in a layer surrounding the core. In each case, the tablet may further comprise a water-soluble, water-insoluble, or enteric coating surrounding the outer layer.

Enteric and other pH-sensitive polymers which are relatively insoluble and impermeable at the pH of the stomach, but which are more soluble and permeable at the pH of the small intestine and colon include polyacrylamides, phthalate derivatives such as acid phthalates of carbohydrates, amylose acetate phthalate, cellulose acetate phthalate, other cellulose ester phthalates, cellulose ether phthalates, hydroxypropylcellulose phthalate, hydroxypropylethylcellulose phthalate, hydroxypropylmethylcellulose phthalate, methylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, styrene and maleic acid copolymers, polyacrylic acid derivatives such as acrylic acid and acrylic ester copolymers, polymethacrylic acid and esters thereof, poly acrylic methacrylic acid copolymers, shellac, and vinyl acetate and crotonic acid copolymers. Preferred pH-sensitive polymers include shellac; phthalate derivatives, particularly cellulose acetate phthalate, polyvinylacetate phthalate, and hydroxypropylmethylcellulose phthalate; polyacrylic acid derivatives, particularly polymethyl methacrylate blended with acrylic acid and acrylic ester copolymers; and vinyl acetate and crotonic acid copolymers.

In some embodiments, the antibiotic drug and the probiotic mixture are contained together within a core surrounded by an enteric coating or a delayed release coating. A delayed release coating can be, for example, a coating of a water-insoluble polymer such as ethylcellulose which may be impregnated with water-soluble materials that dissolve in the stomach and create pores in the coating.

In another embodiment, only the probiotic component is encapsulated in an enteric coating which releases the probiotic mixture in the small intestine. These microcapsules of encapsulated probiotic may be combined in a dosage form with the antibiotic which may or may not be encapsulated in an enteric coating or modified release coating material. The antibiotic also may, for example, be provided in the form of microcapsules or the like, with or without a modified-release coating. The microcapsules of probiotic and the microcapsules of antibiotic may be charged into a capsules or may be tableted together. Such an oral dosage form provides release of the antibiotic drug at a first location and/or time in the gastrointestinal tract and release of the probiotic mixture at a second location and/or time in the gastrointestinal tract. This can also be accomplished by selection of the appropriate dosage form, including the use of tablets having multiple layers, including for example, a core comprising the probiotic material, a coating surrounding the core comprising an enteric or delayed release coating, and an external layer comprising the antibiotic for immediate release. Alternatively, the tablet may be an osmotic device comprising a water-insoluble shell having a passage therethrough to permit water from the gut to penetrate the shell and dissolve the carrier contained within the shell, thereby releasing the drug or probiotic contained within the shell. The core may comprise a first carrier, proximal to the passage which releases the antibiotic first, and a second carrier distal to the passage which releases the probiotic only after the antibiotic has been substantially released.

The antibiotic and probiotic may be dispersed in any pharmaceutically acceptable carrier, which may be an immediate release or a slow release carrier. The carrier may comprise micro-crystalline cellulose (MCC), dextran, corn starch, flour, talc, sucrose, mannitol, lactose, calcium carbonate, polyvinylpyrrolidone (PVP), polyethylene oxide, hydroxypropyl methylcellulose (HPMC), hydroxypropylcellulose (HPC), polyvinyl alcohol (PVA) or the like. The carrier will typically be compressed into a core and then coated with a polymeric coating to modify the release profile of the contents. The coating may comprise a water-soluble polymer such as polyvinylpyrrolidone (PVP), polyvinylpolypyrrolidone (crospovidone), or polyethylene glycol, or a water insoluble polymer selected from the group consisting of ethers of cellulose, esters of cellulose, cellulose acetate, ethyl cellulose, polyvinyl acetate, neutral copolymers based on ethylacrylate and methylmethacrylate, copolymers of acrylic and methacrylic acid esters with quaternary ammonium groups, pH-insensitive ammonio methacrylic acid copolymers, and mixtures thereof. The coating may comprise a natural polymer such as methylcellulose, elthylcellulose, hydroxyethyl cellulose, hydroxypropyl methyl cellulose (HPMC), hydroxypropyl cellulose (HPC), or a combination therefore. The use of methylcellulose in combination with hydroxypropyl methyl cellulose (HPMC) is well known.

Standard ingredients and methods of preparation of tablets, including modified release tablets are described in "Remington: The science and practice of pharmacy," (1995), herein incorporated by reference. Additional excipients include, without limitation, lubricants, disintegrants, and the like. The tablets may be scored to permit them to be easily broken into two substantially equal portions to facilitate swallowing.

EXAMPLES

Example 1

A male patient with a clinical diagnosis of chronic ulcerative colitis regularly suffered relapses following a variety of treatments, including Asacol, Purinethol, Colazal, Rifaximin, Remicade, Flagyl, Clindamycin, Cyclosporine, Cipro, Cortifoam, and Budesonide. The chronic condition persisted for about 35 years, failed to go into prolonged remission, and was characterized by frequent relapse. The patient failed all previous protocols and was facing surgical intervention. The patient was administered Septra DS tablets (160 mg trimethoprim and 800 mg sulfamethoxazole) twice daily for 360 days to treat an unrelated vasculitis. Concurrently, the patient orally ingested probiotic capsules (40 billion cells daily), along with Omega-3 fish oil capsules (1,000 mg daily), 50 mg of 6-mercaptopurine daily, and 12 tablets daily of 400 mg Asacol. After 90 days, the colitis symptoms were improved and after 180 days, the patient was in clinical remission. After 180 days, tablets of trimethoprim (160 mg) and sulfamethoxazole (800 mg) were administered once daily for an additional 180 days with continued use of probiotics, 6-mercaptopurine, and Omega-3 fish oil. The patient has been asymptomatic for over three years.

Example 2

Representative tablets according to the invention have the formulation provided in Table 1. These are multi-layer tablets having an immediate-release layer of probiotics around a delayed-release layer of antibiotic. The delayed-release layer of antibiotic is encapsulated in an enteric coating which dissolves at a pH of 7 or greater to ensure that the antibiotic is substantially released in the small intestine, and in particular in the terminal ileum, rather than in the stomach. The tablets may be full-strength, in which case the treatment protocol recommends twice daily administration, or the tablets may be half-strength, in which case four tablets daily are required during the treatment regimen.

TABLE 1

Composition of tablets.

| | full-strength | half-strength |
|---|---|---|
| Delayed-release antibiotic layer | | |
| sulfamethoxazole | 800 mg | 400 mg |
| trimethoprim | 160 mg | 80 mg |
| Immediate-release probiotic layer | | |
| Bifidobacterium bifidum | ~5 billion cells | ~2.5 billion cells |
| Bifidobacterium breve | ~2 billion cells | ~1 billion cells |
| Bifidobacterium infantis | ~2 billion cells | ~1 billion cells |
| Bifidobacterium longum | ~2 billion cells | ~1 billion cells |
| Lactobacillus acidophilus | ~5 billion cells | ~2.5 billion cells |
| Lactobacillus bulgaricus | ~500 million cells | ~250 million cells |
| Lactobacillus paracasein | ~2 billion cells | ~1 billion cells |
| Saccharomyces boulardii | ~2.5 billion cells | ~1.75 billion cells |

A treatment protocol according to the invention includes a first treatment step during the active phase of disease and, after clinical remission, a prophylaxis step to reduce the likelihood of recurrence of symptoms. A representative treatment regimen is as follows:

Treatment: 1 full-strength tablet, every 12 hours for 180 days.

Maintenance and Prophylaxis: 1 full-strength tablet, daily for 90 days.

Of course, it will be recognized that the treatment regimen may be modified if the half-strength tablets are used by administering two of such tablets in place of each full-strength tablet. The treatment regimen also allows for decreased levels of immunosuppressants (antimetabolites) and, if it is feasible to do so without adverse reactions, the total elimination of immunosuppressants. An anti-inflammatory such as mesalamine (Asacol or Lialda) may also be used in conjunctions with the antibiotic/probiotic therapy. For example, six 400 mg Asacol tablets may be administered twice daily for the duration of the treatment regimen. The treatment may further include the following dietary adjustments:

Fish oil capsules, Omega-3, 1000 mg, 1 tablet 2× daily for 180 days.

Limit alcohol and refined sugar intake for 90 days.

Eliminate gluten, wheat, whey, red meat and dairy for 90 days.

Limit fat intake for 90 days.

Reduce or eliminate folic acid and/or iron supplements.

All patents and patent publications referred to herein are hereby incorporated by reference. Certain modifications and improvements will occur to those skilled in the art upon a reading of the foregoing description. It should be understood that all such modifications and improvements have been deleted herein for the sake of conciseness and readability but are properly within the scope of the following claims.

I claim:

1. An oral dosage form for the treatment of inflammatory bowel disease due to bacterial infection, said dosage form comprising:
   (i) a delayed-release component comprising an amount of antibiotic effective to reduce colonization of pathogenic bacteria in the gastrointestinal tract, said antibiotic comprising a combination of sulfamethoxazole and trimethoprim; and
   (ii) an immediate-release component comprising a probiotic formulation in an amount effective to restore normal microflora colonies in the gut;
   wherein said immediate-release component releases said probiotic formulation upon contact with fluid in the stomach; and wherein said delayed-release component releases said antibiotic at a pH of 7 or greater.

2. The oral dosage form according to claim 1, wherein said probiotic formulation comprises at least one strain selected from the group consisting of *Bifidobacterium bifidum*; *Bifidobacterium breve*; *Bifidobacterium infantis*; *Bifidobacterium longum*; *Lactobacillus acidophilus*; *Lactobacillus bulgaricus*; *Lactobacillus paracasei*; *Saccharomyces boulardii*, and combinations thereof.

3. The oral dosage form according to claim 1, wherein said antibiotic comprises from about 200 mg to about 800 mg of sulfamethoxazole and from about 40 mg to about 160 mg of trimethoprim.

4. The oral dosage form according to claim 2, wherein said antibiotic comprises about 800 mg of sulfamethoxazole and about 160 mg of trimethoprim and wherein said probiotic formulation comprises at least about 10 billion cells.

5. The oral dosage form according to claim 3, wherein said probiotic formulation comprises:
   about 5 billion cells of *Bifidobacterium bifidum*;
   about 2 billion cells of *Bifidobacterium breve*;
   about 2 billion cells of *Bifidobacterium infantis*;
   about 2 billion cells of *Bifidobacterium longum*;
   about 5 billion cells of *Lactobacillus acidophilus*;
   about 500 million cells of *Lactobacillus bulgaricus*;
   about 2 billion cells of *Lactobacillus paracasei*; and
   about 2.5 billion cells of *Saccharomyces boulardii*.

6. The oral dosage form according to claim 2, wherein said antibiotic comprises about 400 mg of sulfamethoxazole and about 80 mg of trimethoprim and wherein said probiotic formulation comprises at least about 5 billion cells.

7. The oral dosage form according to claim 3, wherein said probiotic formulation comprises:
   about 2.5 billion cells of *Bifidobacterium bifidum*;
   about 1 billion cells of *Bifidobacterium breve*;
   about 1 billion cells of *Bifidobacterium infantis*;
   about 1 billion cells of *Bifidobacterium longum*;
   about 2.5 billion cells of *Lactobacillus acidophilus*;
   about 250 million cells of *Lactobacillus bulgaricus*;
   about 1 billion cells of *Lactobacillus paracasei*; and
   about 1.75 billion cells of *Saccharomyces boulardii*.

8. A method for the treatment of inflammatory bowel disease due to bacterial infection comprising administering to a patient in need thereof, an oral dosage form comprising:
   (i) a delayed-release component comprising an amount of antibiotic effective to reduce colonization of pathogenic bacteria in the gastrointestinal tract, said antibiotic comprising:
   from about 200 mg to about 800 mg of sulfamethoxazole; and
   from about 40 mg to about 160 mg of trimethoprim; and
   (ii) an immediate-release component comprising a probiotic formulation in an amount effective to restore normal microflora colonies in the gut;
   wherein said immediate-release component releases said probiotic formulation upon contact with fluid in the stomach; and wherein said delayed-release component releases said antibiotic at a pH of 7 or greater.

9. The method according to claim 8, wherein said delayed-release component releases said antibiotic in the small intestine.

10. The method according to claim 9, wherein said delayed-release component releases said antibiotic primarily in the terminal ileum.

11. The method according to claim 8, wherein said probiotic formulation comprises at least one strain selected from the group consisting of *Bifidobacterium bifidum; Bifidobacterium breve; Bifidobacterium infantis; Bifidobacterium longum; Lactobacillus acidophilus; Lactobacillus bulgaricus; Lactobacillus paracasei; Saccharomyces boulardii*, and combinations thereof.

12. The method according to claim 8, wherein said oral dosage form comprises about 400 mg to about 800 mg of sulfamethoxazole and from about 80 mg to about 160 mg of trimethoprim.

13. The method according to claim 8, wherein said oral dosage form comprises about 800 mg of sulfamethoxazole and about 160 mg of trimethoprim and wherein said probiotic formulation comprises at least about 10 billion cells.

14. The method according to claim 8, wherein said oral dosage form comprises:
    about 5 billion cells of *Bifidobacterium bifidum;*
    about 2 billion cells of *Bifidobacterium breve;*
    about 2 billion cells of *Bifidobacterium infantis;*
    about 2 billion cells of *Bifidobacterium longum;*
    about 5 billion cells of *Lactobacillus acidophilus;*
    about 500 million cells of *Lactobacillus bulgaricus;*
    about 2 billion cells of *Lactobacillus paracasei;* and
    about 2.5 billion cells of *Saccharomyces boulardii.*

15. The method according to claim 8, wherein said oral dosage form comprises about 400 mg of sulfamethoxazole and about 80 mg of trimethoprim and wherein said probiotic formulation comprises at least about 5 billion cells.

16. The method according to claim 8, wherein said probiotic formulation comprises:
    about 2.5 billion cells of *Bifidobacterium bifidum;*
    about 1 billion cells of *Bifidobacterium breve;*
    about 1 billion cells of *Bifidobacterium infantis;*
    about 1 billion cells of *Bifidobacterium longum;*
    about 2.5 billion cells of *Lactobacillus acidophilus;*
    about 250 million cells of *Lactobacillus bulgaricus;*
    about 1 billion cells of *Lactobacillus paracasei;* and
    about 1.75 billion cells of *Saccharomyces boulardii.*

17. The method according to claim 8, wherein said step of administering comprises:
    twice daily administration for a period from 120 to 180 days for the treatment of active symptoms.

18. A method for the treatment of inflammatory bowel disease due to bacterial infection comprising administering to a patient in need thereof, an oral dosage form comprising:
    (i) a delayed-release component comprising an amount of antibiotic effective to reduce colonization of pathogenic bacteria in the gastrointestinal tract, said antibiotic comprising:
        from about 200 mg to about 800 mg of sulfamethoxazole; and
        from about 40 mg to about 160 mg of trimethoprim; and
    (ii) an immediate-release component comprising a probiotic formulation in an amount effective to restore normal microflora colonies in the gut;
wherein said immediate-release component releases said probiotic formulation upon contact with fluid in the stomach; and wherein said delayed-release component releases said antibiotic in the small intestine.

\* \* \* \* \*